United States Patent
Yan et al.

(10) Patent No.: US 11,083,824 B2
(45) Date of Patent: Aug. 10, 2021

(54) COMPOUND HEPARIN ANTICOAGULANT COATING LIQUID, A MICROSPHERE FOR COATING AND ITS PREPARATION METHODS AND APPLICATIONS

(71) Applicant: WUHAN YOUNGSEN BIOTECH CO., LTD, Wuhan (CN)

(72) Inventors: Tuo Yan, Wuhan (CN); Chenxi Ouyang, Wuhan (CN); Yawen Liu, Wuhan (CN); Sishi Liu, Wuhan (CN); Yuan Liu, Wuhan (CN)

(73) Assignee: WUHAN YOUNGSEN BIOTECH CO., LTD, Wuhan (CN)

( * ) Notice: Subject to any disclaimer, the term of this patent is extended or adjusted under 35 U.S.C. 154(b) by 0 days.

(21) Appl. No.: 16/691,688

(22) Filed: Nov. 22, 2019

(65) Prior Publication Data
US 2020/0086012 A1    Mar. 19, 2020

Related U.S. Application Data

(63) Continuation of application No. PCT/CN2018/102568, filed on Aug. 27, 2018.

(30) Foreign Application Priority Data

Aug. 28, 2017 (CN) .......................... 201710748805.8
Aug. 28, 2017 (CN) .......................... 201710748820.2

(51) Int. Cl.
*A61L 33/00* (2006.01)
*A61L 33/04* (2006.01)
*A61L 33/12* (2006.01)

(52) U.S. Cl.
CPC .......... *A61L 33/0011* (2013.01); *A61L 33/04* (2013.01); *A61L 33/128* (2013.01); *A61L 2300/42* (2013.01)

(58) Field of Classification Search
None
See application file for complete search history.

(56) References Cited

U.S. PATENT DOCUMENTS

2014/0112973 A1* 4/2014 Steinberg ................ A61L 27/50
424/445

FOREIGN PATENT DOCUMENTS

| CN | 102988999 A | 3/2013 |
|---|---|---|
| CN | 103566414 A | 2/2014 |

OTHER PUBLICATIONS

Shim et al (Irreversible Inhibition of CD13/Aminopeptidase N by the Antiangiogenic Agent Curcumin. Chemistry & Biology, vol. 10, 695-704, Aug. 2003) (Year: 2003).*

* cited by examiner

*Primary Examiner* — Jake M Vu

(57) ABSTRACT

The present invention discloses a compound heparin anticoagulant coating liquid, a microsphere for coating and its preparation methods and applications. In the present invention, the combination of curcumin and heparin can enhance the anticoagulation functions of heparin coating, and further enhance the stability using the properties of PLA-PEG-PLA drug-loaded sustained-release microspheres, achieving the functions of anti-tissue proliferation and anti-inflammatory reactions that cannot be achieved by coatings alone such as heparin or protein, which is very important for implanted devices such as artificial blood vessels, vascular stents and vascular patches to reduce thrombosis in the human body, lower postoperative complications and improve product lifespan.

2 Claims, No Drawings

COMPOUND HEPARIN ANTICOAGULANT COATING LIQUID, A MICROSPHERE FOR COATING AND ITS PREPARATION METHODS AND APPLICATIONS

CROSS-REFERENCE TO RELATED APPLICATIONS

The present application is a continuation-application of International Patent Application (PCT) No. PCT/CN2018/102568 filed on Aug. 27, 2018, which claims foreign priorities of Chinese Patent Application No. 201710748820.2, filed on Aug. 28, 2017, and Chinese Patent Application No. 201710748805.8, filed on Aug. 28, 2017, the entire contents of which are hereby incorporated by reference.

TECHNICAL FIELD

The present invention relates to a compound heparin anticoagulant coating liquid, a microsphere for coating and its preparation methods and applications, and belongs to the field of biomedical materials technology.

BACKGROUND ART

With the improvement of people's living standards, cardiovascular diseases such as atherosclerosis, vascular embolism and aneurysms have caused great threats to human health. When human body's blood vessels cannot supply blood normally due to the above diseases, artificial blood vessels are required for surgical replacement surgery. Blood vessels in human body have a diameter ranging from 2 mm to 30 mm. Of which, blood vessels with small diameter (diameter <6 mm) are prone to intimal hyperplasia and thrombosis, which lead to low patency rate of small-diameter vessels. At present, most of the artificial blood vessel materials used for operations in hospitals are ePTFE, PU, etc., but these materials do not have good anticoagulant properties, and it is necessary to perform anticoagulant coatings on the surfaces of materials.

At present, commonly used anticoagulant coatings include heparin coating, with varied coating methods. The heparin coating materials prepared by different methods have different properties.

SUMMARY

The object of the present invention is to provide a compound heparin anticoagulant coating liquid, a microsphere for coating, and its preparation methods and applications. The object includes two parts: the first part is a compound heparin anticoagulant coating liquid and its preparation method and application, and the second part is a microsphere for compound heparin anticoagulant coating, its preparation method and application.

In order to achieve the first part, the present invention provides a compound heparin anticoagulant coating liquid, which comprises a hydrazinocurcumin-heparin in a crosslinked state.

The effective part in the compound heparin anticoagulant coating liquid of the present invention is hydrazinocurcumin-heparin, and the hydrazinocurcumin is crosslinked with heparin via an amino group thereon.

The present invention further provides a preparation method of the above compound heparin anticoagulant coating liquid, comprising the following steps:

Dissolving hydrazinocurcumin in ethanol solution to prepare curcumin solution, adding MES buffer solution to curcumin solution, then adding heparin, and then adding EDC and NHS crosslinking agent, stirring for 1~2 h, to make amino group in hydrazinocurcumin to fully react with heparin, and then placing the solution after reaction into a dialysis bag for dialysis for 24~72 h, after completion of dialysis, a compound heparin anticoagulant coating liquid is obtained.

In the above method, the weight ratio of the hydrazinocurcumin to the heparin is from 1~10:40, This ratio is a preferred reaction ratio of hydrazinocurcumin and heparin. The active ingredient in the present invention is hydrazinocurcumin-heparin in a crosslinked state, so any ratio of hydrazinocurcumin and heparin which can produce hydrazinocurcumin-heparin can be used.

It should be noted that the above coating liquid is not effective when used alone, and it is effective only when combined with a biologically active protein, such as collage, silk fibroin and fibronectin. Through studies, the inventor found that the combination of hydrazinocurcumin-heparin and silk fibroin at a certain ratio can achieve a better effect.

Accordingly, the present invention further provides a bio-anticoagulation coating liquid of hydrazinocurcumin-heparin and silk fibroin, and the bio-anticoagulation coating liquid comprises a cross-linked hydrazinocurcumin-heparin, and a silk fibroin; the concentration of the hydrazinocurcumin-heparin in the bio-anticoagulation coating liquid is 0.5% to 5% by weight, the concentration of the silk fibroin is 5% to 15% by weight, and the concentration ratio of hydrazinocurcumin-heparin to silk fibroin is 1:1 to 1:10.

In order to achieve the second part, the present invention provides a microsphere for compound heparin anticoagulant coating, which comprises a PLA-PEG-PLA and a cross-linked hydrazinocurcumin-heparin, the PLA-PEG-PLA is used as a carrier and the crosslinked hydrazinocurcumin-heparin is content.

The hydrazinocurcumin is crosslinked with heparin via an amino group thereon.

The present invention further provides a preparation method of the microsphere for compound heparin anticoagulant coating, comprising the following steps:

1) Dissolving hydrazinocurcumin in ethanol solution to prepare curcumin solution, adding MES buffer solution to curcumin solution, then adding heparin, and then adding EDC and NHS crosslinking agent, stirring for 1~2 h, to make amino group in hydrazinocurcumin to fully react with heparin, and then placing the solution after reaction into a dialysis bag for dialysis for 24~72 h, after completion of dialysis, a compound heparin anticoagulant coating liquid is obtained;

2) Preparing the resulting compound heparin anticoagulant coating liquid into a lyophilized powder using the PLA-PEG-PLA as a material, then emulsifying the lyophilized powder together with PLA-PEG-PLA to prepare a microsphere.

In the above preparation method, the weight ratio of the hydrazinocurcumin to the heparin is from 1~10:40. This ratio is a preferred reaction ratio of hydrazinocurcumin and heparin. The active ingredient in the present invention is hydrazinocurcumin-heparin in a crosslinked state, so any ratio of hydrazinocurcumin and heparin which can produce hydrazinocurcumin-heparin can be used.

It should be noted that the above microsphere for compound heparin anticoagulant coating is not effective when used alone as a coating liquid, and it is effective only when combined with a biologically active protein, such as collage, silk fibroin and fibronectin. Through studies, the inventor found that the combination of hydrazinocurcumin-heparin and silk fibroin at a certain ratio can achieve a better effect.

Accordingly, the present invention further provides a silk fibroin compound heparin microsphere anticoagulation microsphere coating liquid, and the coating liquid comprises the microsphere for compound heparin anticoagulant coating and the silk fibroin encapsulating the microsphere; the concentration of the silk fibroin is 5~5% by weight, and the concentration ratio of the microsphere for compound heparin anticoagulant coating to silk fibroin is 1:1~10.

The present invention binds the curcumin that has properties of anti-tissue proliferation and anti-inflammatory reactions with heparin (the bio-anticoagulation stability can be improved using the properties of PLA-PEG-PLA drug-loaded sustained-release microspheres), to overcome the events that may happen for implanted medical devices (for example, artificial blood vessels) after implantation in human body (for example, blood coagulation may lead to platelet aggregation and cause thrombus and vascular restenosis, while tissue hyperplasia and inflammatory reactions may cause rejection reaction and vascular stenosis, which eventually deteriorates the biocompatibility of implanted devices such as artificial blood vessels and fails to implant).

Beneficial Effects

Modern pharmacological studies have shown that curcumin components have various pharmacological effects such as anticoagulation, anti-tissue proliferation, and anti-inflammatory reactions. In the present invention, the combination of curcumin and heparin can enhance the anticoagulation functions of heparin coating, and further enhance the stability using the properties of PLA-PEG-PLA drug-loaded sustained-release microspheres, achieving the functions of anti-tissue proliferation and anti-inflammatory reactions that cannot be achieved by coatings alone such as heparin or protein, which is very important for implanted devices such as artificial blood vessels, vascular stents and vascular patches to reduce thrombosis in the human body, lower postoperative complications and improve product lifespan.

DETAILED DESCRIPTION OF THE EMBODIMENTS

The present invention is further described in detail below with reference to specific embodiments.

It should be noted that the artificial blood vessels (ePTFE) used in the following embodiments are subjected to pretreatment before coating, to enhance the adhesion to the coating, so that the bio-coating can exert its anticoagulant functions stably and effectively.

The pretreatment process of artificial blood vessel (ePTFE) substrate is as follow:

First Layer

The ePTFE artificial blood vessels are immersed in isopropyl alcohol (IPA) for 5~10 min, then taken out with tweezers and immersed in 4% polyethyleneimine (PEI) and IPA mixture (volume ratio of PEI to IPA=1:1) for 15~30 min; then the soaked artificial blood vessels are taken out, and rinsed with deionized water. After rinsing, the artificial blood vessels are placed in a 0.05% glutaraldehyde solution for cross-linking for 15~20 min. After the reaction is completed, the artificial blood vessels are again immersed in 0.5% PEI solution for 15~30 min, and immersed and rinsed using deionized water. After rinsing, the artificial blood vessels are immersed in a sodium cyanoborohydride solution for 15~30 min, and rinsed with deionized water after the reaction is completed.

Second Layer

The above treated artificial blood vessels are immersed in a 0.05% glutaraldehyde solution for crosslinking, and after the reaction is completed, the artificial blood vessels are again immersed in 0.5% PEI solution, and the constructed artificial blood vessels are immersed and rinsed with deionized water. After the rinsing is completed, the artificial blood vessels are immersed in a sodium cyanoborohydride solution, and immersed and rinsed with deionized water after the reaction is completed.

Third Layer 0.15 g of dextran sulfate and 100 g of NaCl are dissolved in 1 L of deionized water to form a mixed solution, then the above artificial blood vessels after treatment of the second layer are immersed in the mixed solution to react at 60° C. for 1~2 h. After the reaction is completed, the artificial blood vessels are rinsed with deionized water repeatedly, to prepare an intermediate charge layer.

Fourth Layer

The artificial blood vessels after treatment of the third layer are immersed in 0.3% PEI solution for 0.5~1 h, then immersed and rinsed with 50 g/L sodium chloride solution, and then immersed and rinsed with deionized water to obtain an artificial blood vessel (ePTFE) substrate.

Part One Preparation of Compound Heparin Anticoagulant Coating Liquid and Experiments Embodiment 1 Hydrazinocurcumin-Heparin A compound heparin anticoagulant coating liquid comprises hydrazinocurcumin-heparin in a crosslinked state.

A preparation method of the compound heparin anticoagulant coating liquid, comprising the following steps:

Dissolve hydrazinocurcumin in ethanol solution, to prepare a curcumin solution at a concentration of 5 mg/mL, add MES buffer solution to curcumin solution to reduce the curcumin concentration to 2.5 mg/mL; after adding 10 g heparin to 300 mL curcumin solution, then add 4 g EDC and 4 g NHS, stirring for 1~2 h, to make the amino group in hydrazinocurcumin to fully react with heparin, and then place the solution after reaction into a dialysis bag for dialysis for 24~72 h, after completion of dialysis, a compound heparin anticoagulant coating liquid is obtained. The coating liquid can be freeze-dried to obtain a composite heparin anticoagulant coating lyophilized powder, which can be stored for a long time.

Embodiment 2 Hydrazinocurcumin-Heparin and Silk Fibroin Coating

A method for preparing a bio-anticoagulant coated artificial blood vessel using hydrazinocurcumin-heparin and silk fibroin, comprising the following steps:

1) Dissolve the lyophilized powder prepared in Embodiment 1 in a silk fibroin macromolecular solution, to obtain a mixed coating solution, with a concentration of hydrazinocurcumin-heparin at 1% by weight, and a concentration of silk fibroin at 10% by weight, which is a bio-anticoagulation coating liquid of hydrazinocurcumin-heparin and silk fibroin.

2) Immerse the artificial blood vessel (ePTFE) substrate in resulting bio-anticoagulation coating liquid of Step 1) for 10~30 min, then take out and put it in a ventilated place.

After completely dried, immerse it in 30~75% methanol solution for 2~4 h. After immersion, dry it in a ventilated place.

3) Repeat Step 2) twice to apply the second and third layers of coatings to the artificial blood vessel (ePTFE).

Therein, the preparation method of the silk fibroin in Step 1): put 20~30 g raw silk into 10~12 L of $Na_2CO_3$ (2.12 g/L) solution and boil it with boiled water for 20~30 min, and then repeatedly rinse the boiled degummed silk with deionized water to remove the residual silk gum. Spread the rinsed silk fibroin fibers in a ventilated place for drying. Weigh 15~25 g of dried silk fiber and dissolve in 100~150 mL of LiBr solution (9.3M) at 60° C. After dissolved, use a dialysis bag to dialyze the silk protein solution 36~72 h, and after dialysis, centrifuge the solution to remove impurities, to obtain silk fibroin macromolecular solution.

Embodiment 3 Hydrazinocurcumin-Heparin and Silk Fibroin Coating

This Embodiment is basically the same as Embodiment 2 except that the hydrazinocurcumin-heparin has a concentration of 0.7% by weight and the silk fibroin has a concentration of 5.6% by weight in the bio-anticoagulation coating liquid of hydrazinocurcumin-heparin and silk fibroin.

Embodiment 4 Hydrazinocurcumin-Heparin and Silk Fibroin Coating

This Embodiment is basically the same as Embodiment 2 except that the hydrazinocurcumin-heparin has a concentration of 5% by weight and the silk fibroin has a concentration of 15% by weight in the bio-anticoagulation coating liquid of hydrazinocurcumin-heparin and silk fibroin.

Embodiment 5 Heparin/Poly-L-Lysine Coaling

A heparin/poly-L-lysine coating artificial blood vessel is prepared according to the following steps:

1) Prepare Heparin Macromolecule

Dissolve 0.176 g of poly-L-lysine in 300 mL of MES buffer solution, and add 4 g Sulfo-NH and 4 g HCl-EDC, after the mixture reacts at room temperature for 1 h, add 10 g of heparin sodium powder to react for 4 h, after completion of reaction, dialyze the mixture with a dialysis bag for 24~36 h. After the dialysis is completed, add 10 mg of sodium nitrite and 2 mL of acetic acid to the dialysate to react for 2 h at 0° C. After completion of reaction, continue to dialyze the solution for 24 h. After the dialysis is completed, the solution is frozen and dried to obtain heparin/poly-L-lysine lyophilized powder.

2) Prepare Coating

Dissolve 09 g of heparin/poly-L-lysine lyophilized powder in 200 mL of deionized water to prepare a heparin macromolecular solution. Immerse the treated artificial blood vessel in Embodiment 3 in the heparin macromolecular solution to react at 60° C. for 10~20 min, then add 572 µL of 2.5% sodium cyanoborohydride to continue reaction for 2~3 h. After all reactions are completed, the artificial blood vessel is rinsed off with deionized water and borate buffer solution, and lyophilized.

Embodiment 6 Heparin and Silk Fibroin Coating

A silk fibroin heparin coating artificial blood vessel is prepared according to the following steps:

1) Prepare heparin macromolecule (the same as Embodiment 5) and prepare silk fibroin macromolecular solution (the same as Embodiment 2).

2) Silk Fibroin and Heparin Coating

Mix the silk fibroin macromolecule solution and heparin/poly-L-lysine, to obtain a mixture, with a concentration of silk fibroin at 10% and a concentration of heparin/poly-L-lysine at 4%.

3) Prepare Coating

The first layer: immerse an artificial blood vessel (ePTFE) substrate in the above mixture for 10~30 min, and then take out and place it in a ventilated place. After completely dried, immerse it in 30~75% methanol solutions for 2~4 h, and after immersion, dry it in a ventilated place.

The second layer/third layer: Carry out the same procedure as the first layer.

Embodiment 7 Fibronectin and Heparin Coating

A fibronectin heparin coating artificial blood vessel is prepared according to the following steps:

Mix the fibronectin and heparin/poly-L-lysine, to obtain a mixture, with a concentration of fibronectin at 10~30% by weight and a concentration of heparin/poly-L-lysine at 0.5~5% by weight, then carry out reaction at 37° C. for 1~2 h, and add EDC/NHS/MES crosslinking agent at a molar ratio of 1M:2M:2M and a volume ratio of heparin/PLL to crosslinking agent at 1:2~15. Immerse an artificial blood vessel (ePTFE) substrate in the mixture to react at 37° C. for 1~5 h.

After the above reaction is completed, take 100~1,000 µL of 200 ng/mL SDF-1α to immerse the substrate material to react at 4° C. for 12~24 h; after completion of the reaction, immerse and rinse it with a phosphate buffer solution for 15~30 min, and then immerse and rinse with deionized water for 30 min, and dry.

Embodiment 8 Collagen Coating

A collagen coating artificial blood vessel is prepared according to the following steps:

Prepare the collagen to a concentration of 10~30% by weight with glacial acetic acid, and add heparin lyophilized powder to 200 mL collagen mixture to make the heparin concentration at 0.5~5% by weight. After fully dissolved, immerse an artificial blood vessel (ePTFE) substrate in the mixture, after thoroughly immersed, carry out freeze drying for 24~48 h. After the freeze-drying is completed, perform crosslinking for the collagen by ultraviolet irradiation. After repeated immersion and freeze drying for three times, the surface collagen coating polymer material is obtained.

Embodiment 9 Polydopamine Coating

A polydopamine coating artificial blood vessel is prepared according to the following steps:

Immerse an artificial blood vessel (ePTFE) substrate in an 8 mg/mL dopamine solution to react for 12 h at room temperature, then perform ultrasonic washing in deionized water, and then immerse in the dopamine solution again. After repeating four times, place the artificial blood vessel in 100° C. for heat treatment for 1 h. After the treatment is completed, the artificial blood vessel is rinsed with deionized water and dried at normal temperature.

Experiment Embodiment 1 Cytotoxicity Test

The cytotoxicity of a coating artificial blood vessel is detected by an extraction method according to the following steps:

1) Take a coating artificial blood vessel or coating material prepared in Comparative Embodiment and Embodiments 2~9 and extract it using 0.2 g/mL high-glucose cell culture medium containing fetal bovine serum for 24~72 h.

2) Take cells in the normal growth log phase (NH/3T3), perform cell dissociation and blowing, prepare a cell suspension at a concentration of $1\times10^5$ cells/mL, and then inoculate in a 96-well plate, 100 per well. After being placed in a carbon dioxide constant temperature incubator for 24 h, discard the original culture solution.

3) Add DMEM complete medium (blank group), polyethylene extract (negative control), 5% DMSO medium (positive control), and artificial blood vessel sample extract (sample group) separately in each group. Continue to culture for 24 h, discard the liquid in the wells.

4) Add 10 µL of 5 mg/mL MTT solution to each well to react, and continue culture and incubation in the incubator for 4 h.

5) Add 100 µL of Formanzan solution to each well and continue incubating in a cell culture incubator until Formanzan is dissolved completely under a light microscope.

6) Place the 96-well plate on a microplate reader measure the absorbance value at 570 nm.

Calculate the relative growth degree (RGD) of cells according to the concentration of each group of cells:

RGD=Mean cell concentration of test sample group (or positive control group)/Mean cell concentration of negative control group×100%

TABLE 1

| Classification Table of Relative Growth Degree (RGD) | |
| --- | --- |
| Classification | Relative Growth Degree (RGD, %) |
| 0 | ⩾ 100 |
| 1 | 75~99 |
| 2 | 50~74 |
| 3 | 25~49 |
| 4 | 1~24 |
| 5 | 0 |

Experimental results:

TABLE 2

| Cytotoxicity Test Results of Each Group | | |
| --- | --- | --- |
| Group | RGD (100%) | Toxicity Classification |
| Blank control group | 100 | 0 |
| Negative control group | 100 | 0 |
| Positive control group | 8 | 4 |
| Embodiment 2 | 92 | 1 |
| Embodiment 3 | 91 | 1 |
| Embodiment 4 | 90 | 1 |
| Embodiment 5 | 92 | 1 |
| Embodiment 6 | 89 | 1 |
| Embodiment 7 | 87 | 1 |
| Embodiment 8 | 85 | 1 |
| Embodiment 9 | 89 | 1 |

Experiment Embodiment 2: Experiment on Coagulation Time

1) Experiment of partial thromboplastin time (APTT): Take a coating artificial blood vessel prepared in Embodiments 2~9, and add 100~200 µL of platelet-poor plasma and carry out water bath at 37° C. for 0.5 h. After completion of heating, add 100~200 µL of partial thromboplastin solution and 100 µL calcium chloride solution, after mixing well, detect the APTT using an automatic coagulation apparatus.

2) Experiment of prothrombin time (PT): add 100~200 µL of platelet-poor plasma to the artificial blood vessel sample and incubate at 37° C. for 0.5 h. After completion of heating, add PT reagent, and then detect the PT using an automatic coagulation apparatus.

3) Experiment of thrombin time (TT): add 100~200 µL of platelet-poor plasma to the artificial blood vessel sample and incubate at 37° C. for 0.5 h. After completion of heating, add TT reagent, and then detect the TT using an automatic coagulation apparatus.

TABLE 3

| Results of Coagulation Time of Artificial Blood Vessel or Material with and without Coating | | | |
| --- | --- | --- | --- |
| Samples | APTT | PT | TT |
| Normal plasma | 33.5 ± 1.3 | 12.8 ± 0.2 | 15 ± 0.3 |
| Uncoated artificial blood vessel | 34.1 ± 1.1 | 12.6 ± 0.3 | 14.8 ± 0.1 |
| Embodiment 2 | 55.5 ± 0.2 | 22.9 ± 0.2 | 26.2 ± 0.5 |
| Embodiment 3 | 51.5 ± 0.1 | 20.6 ± 0.3 | 24.2 ± 0.1 |
| Embodiment 4 | 52.5 ± 0.3 | 20.9 ± 0.1 | 25.1 ± 0.3 |
| Embodiment 5 | 42.6 ± 0.3 | 17.8 ± 0.4 | 19.2 ± 0.3 |
| Embodiment 6 | 40.5 ± 0.2 | 16.1 ± 0.1 | 18.7 ± 0.2 |
| Embodiment 7 | 41.2 ± 0.1 | 16.2 ± 0.3 | 18.8 ± 0.2 |
| Embodiment 8 | 41.4 ± 0.3 | 16.6 ± 0.6 | 18.1 ± 0.2 |
| Embodiment 9 | 39.9 ± 0.2 | 15.8 ± 0.4 | 17.9 ± 0.1 |

As shown in Table 3, the coagulation time of uncoated artificial blood vessels is similar to that of normal plasma. After coated by curcumin-heparin silk fibroin mixed solution (Embodiments 2~4), the coagulation time is significantly higher than that of uncoated artificial blood vessel, and the APTT is longer by about 3~16 s, the PT is longer by about 4~7 s, and the TT is longer by about 5~8 s compared to other substrate artificial blood vessels. The above experiment shows that, the curcumin-heparin coated artificial blood vessels have greater obvious anticoagulation properties than uncoated artificial blood vessels; and have more anticoagulation properties compared to other artificial blood vessels using heparin and macromolecular protein coatings, suggesting that the combination of curcumin and heparin can enhance anticoagulant effect and the effect of coating is better.

Part Two Preparation of Microsphere for Compound Heparin Anticoagulant Coating and Experiments Embodiment 10 Microsphere for Compound Heparin Anticoagulant Coating A microsphere for compound heparin anticoagulant coating is a microsphere in which PLA-PEG-PLA is used as a carrier and a crosslinked hydrazinocurcumin-heparin as content.

1) For the preparation method of the microsphere for compound heparin anticoagulant coating, the compound heparin anticoagulant coating lyophilized powder is prepared by the method of Embodiment 1.

2) Weigh compound heparin anticoagulant coating lyophilized powder and PLA-PEG-PLA at a weight ratio of 1:1 and dissolve them in a dichloromethane beaker, stir them for 10~30 min to dissolve the mixture completely, and then add emulsifier PVA aqueous solution to continue stirring for 30~60 min, then draw the liquid phase with microspheres, drip it to 500~1,000 mL of ultrapure water, continue stirring, and then perform rinsing and drying. After rinsing 3 times, centrifuge at a high speed to collect the microsphere precipitate at the bottom of the solution, and then perform freeze drying to collect the microsphere, to obtain a microsphere for compound heparin anticoagulant coating.

Embodiment 11 Anticoagulant Coating of Silk Fibroin Composite Heparin Microsphere A method for preparing an artificial blood vessel of anticoagulant coating of silk fibroin composite heparin microsphere, comprising the following steps:

1) Prepare silk fibroin: The procedure is the same as that in Embodiment 2.
2) Dissolve the microsphere for compound heparin anticoagulant coating prepared in Embodiment 10 in a silk fibroin macromolecular solution, to obtain a mixed coating solution, with a concentration of microsphere for compound heparin anticoagulant coating at 1% by weight and a concentration of silk fibroin at 10% by weight, which is an anticoagulant coating liquid of silk fibroin complex heparin microsphere, ultrasonically oscillate the coating liquid for 30 to 60 s to change the structure of silk fibroin.
3) Immerse the artificial blood vessel (ePTFE) substrate in the resulting anticoagulant coating liquid of silk fibroin complex heparin microsphere for 10~30 min, then take out and put it in a ventilated place. After completely dried, immerse it in 30~75% methanol solution for 2~4 h. After immersion, dry it in a ventilated place.
4) Repeat Step 3) twice to apply the second and third layers of coatings to the artificial blood vessel (ePTFE).

Embodiment 12 Anticoagulant Coating of Silk Fibroin Composite Heparin Microsphere This Embodiment is basically the same as Embodiment 11 except that the microsphere for compound heparin anticoagulant coating has a concentration of 0.7% by weight and the silk fibroin has a concentration of 5.6% by weight in the anticoagulant coating liquid of silk fibroin composite heparin microsphere.

Embodiment 13 Anticoagulant Coating of Silk Fibroin Composite Heparin Microsphere This Embodiment is basically the same as Embodiment 11 except that the microsphere for compound heparin anticoagulant coating has a concentration of 0.7% by weight and the silk fibroin has a concentration of 15%% by weight in the anticoagulant coating liquid of silk fibroin composite heparin microsphere.

Experiment Embodiment 3 Cytotoxicity Test

Using Comparative Embodiment and Embodiments 11~13 and 5~9 as research objects, the cytotoxicity of a coating artificial blood vessel is detected by an extraction method according to the experimental procedures of Experiment Embodiment 1.

TABLE 4

Classification Table of Relative Growth Degree (RGD)

| Classification | Relative Growth Degree (RGD, %) |
|---|---|
| 0 | ≥100 |
| 1 | 75~99 |
| 2 | 50~74 |
| 3 | 25~49 |
| 4 | 1~24 |
| 5 | 0 |

Experimental results:

TABLE 5

Cytotoxicity Test Results of Each Group

| Group | RGD (100%) | Toxicity Classification |
|---|---|---|
| Blank control group | 100 | 0 |
| Negative control group | 100 | 0 |
| Positive control group | 8 | 4 |
| Embodiment 11 | 92 | 1 |
| Embodiment 12 | 91 | 1 |
| Embodiment 13 | 90 | 1 |
| Embodiment 5 | 92 | 1 |
| Embodiment 6 | 89 | 1 |
| Embodiment 7 | 87 | 1 |
| Embodiment 8 | 85 | 1 |
| Embodiment 9 | 89 | 1 |

Experiment Embodiment 4: Experiment on Coagulation Time

Using Comparative Embodiment and Embodiments 11~13 and 5~9 as research objects, the coagulation time is tested according to the experimental procedures of Experiment Embodiment 2.

TABLE 6

Results of Coagulation Time of Artificial Blood Vessel or Material with and Without Coating

| Samples | APTT | PT | IT |
|---|---|---|---|
| Normal plasma | 33.5 ± 1.3 | 12.8 ± 0.2 | 15 ± 0.3 |
| Uncoated artificial blood vessel | 34.1 ± 1.1 | 12.6 ± 0.3 | 14.8 ± 0.1 |
| Embodiment 11 | 57.3 ± 0.2 | 24.5 ± 0.2 | 28.4 ± 0.4 |
| Embodiment 12 | 53.6 ± 0.1 | 22.7 ± 0.2 | 26.2 ± 0.1 |
| Embodiment 13 | 55.5 ± 0.1 | 22.4 ± 0.2 | 27.2 ± 0.5 |
| Embodiment 5 | 42.6 ± 0.3 | 17.8 ± 0.4 | 19.2 ± 0.3 |
| Embodiment 6 | 40.5 ± 0.2 | 16.1 ± 0.1 | 18.7 ± 0.2 |
| Embodiment 7 | 41.2 ± 0.1 | 16.2 ± 0.3 | 18.8 ± 0.2 |
| Embodiment 8 | 41.4 ± 0.3 | 16.6 ± 0.6 | 18.1 ± 0.2 |
| Embodiment 9 | 39.9 ± 0.2 | 15.8 ± 0.4 | 17.9 ± 0.1 |

As shown in Table 3 and Table 6, the coagulation time of uncoated artificial blood vessels is similar to that of normal plasma. After coated by curcumin-heparin silk fibroin mixed solution (Embodiments 11~13), the coagulation time is significantly higher than that of uncoated artificial blood vessel, and the APTT is longer by about 11~18 s, the PT is longer by about 5~9 s, and the TT is longer by about 7~11 s compared to other substrate artificial blood vessels. The above experiment shows that, the curcumin-heparin coated artificial blood vessels have more obvious anticoagulation properties than uncoated artificial blood vessels; and have greater anticoagulation properties compared to other artificial blood vessels using heparin and macromolecular protein coatings, suggesting that the combination of curcumin and heparin can enhance anticoagulant effect and the effect of coating is better.

In the foregoing embodiments of the present invention, the ePTFE artificial blood vessel is used as a substrate, in fact, other materials such as PU, PE, polyester, polylactic acid, polysilicone, polyglycolic acid, and silicone rubber can also be coated by the coating liquid of the present invention. As long as the substrate is well processed, the bio-coating can be bound stably and a better coagulation effect can also be achieved.

What is claimed is:

1. A bio-anticoagulation coating liquid of hydrazinocurcumin-heparin and silk fibroin, which comprises a cross-linked hydrazinocurcumin-heparin, and a silk fibroin; the concentration of the hydrazinocurcumin-heparin in the bio-anticoagulation coating liquid is 0.5% to 5% by weight, the concentration of the silk fibroin is 5% to 15% by weight, and the concentration ratio of hydrazinocurcumin-heparin to silk fibroin is 1:1 to 1:10.

2. The bio-anticoagulation coating liquid according to claim 1, wherein the hydrazinocurcumin is crosslinked with heparin via an amino group thereon.

* * * * *